United States Patent [19]

Kim

[11] 4,418,203

[45] Nov. 29, 1983

[54] PROCESS FOR THE EPOXIDATION OF OLEFINS

[75] Inventor: Leo Kim, Alamo, Calif.

[73] Assignee: Shell Oil Company, Houston, Tex.

[21] Appl. No.: 332,425

[22] Filed: Dec. 21, 1981

[51] Int. Cl.$^3$ ............................................. C07D 301/12
[52] U.S. Cl. .................................................. 549/531
[58] Field of Search ......................................... 549/531

[56] References Cited

U.S. PATENT DOCUMENTS 3,806,467 4/1974 Watanabe et al. .................. 549/531
4,024,165 5/1977 Shryne et al. ....................... 549/531

FOREIGN PATENT DOCUMENTS 1399639 7/1975 United Kingdom .

Primary Examiner—Norma S. Milestone

[57] ABSTRACT

A process for the epoxidation of olefins wherein an olefin is contacted with hydrogen peroxide in a fluorinated alcoholic solvent in which are dissolved a catalyst selected from a group consisting of molybdenum, tungsten and rhenium and an organo tin co-catalyst.

5 Claims, No Drawings

PROCESS FOR THE EPOXIDATION OF OLEFINS

FIELD OF THE INVENTION

This invention relates to a process for the epoxidation of olefins by hydrogen peroxide in a fluorinated alcoholic solvent in the presence of soluble molybdenum, tungsten and/or rhenium catalysts and an organic tin, arsenic, antimony and/or germanium co-catalyst.

BACKGROUND OF THE INVENTION

U.S. Pat. No. 3,806,467, issued Apr. 23, 1974 to Watanabe et al. generally discloses the use of alcohols as solvents for epoxidation when hydrogen peroxide is used as a reactant. Particularly disclosed are straight-chain alcohols, polyhydric alcohols and cyclic alcohols as preferred solvents.

U.S. Pat. No. 4,024,165, issued May 17, 1977 to Shryne et al. discloses the use of certain secondary fluorinated alcoholic solvents, such as for example, hexafluoro and perfluoromethyl perfluoroethyl carbinol, as solvents for the epoxidation of olefins using hydrogen peroxide.

The epoxides made by the instant process may be utilized in the production of certain polymers such as polyoxyethylene and polyoxypropylene or as resins forming monomers such as epichlorohydrin.

SUMMARY OF THE INVENTION

This invention relates to a process for the production of epoxides by contacting an olefin with hydrogen peroxide in a fluorinated alcoholic solvent in the presence of a soluble catalyst selected from the group consisting of molybdenum, tungsten and rhenium and a soluble organo co-catalyst selected from the group consisting of organo tin, organo arsenic, organo antimony and organo germanium. The fluorinated alcohol solvent has the general formula $CF_3(CF_2)_nCH_2OH$ wherein n ranges from 0 to about 10. The alcoholic organic solvent utilized in the instant invention is one in which all of the reactants and catalysts are soluble. The use of the instant alcoholic solvent provides for higher conversions of the olefins than the does the prior art solvents.

DESCRIPTION OF THE PREFERRED EMBODIMENTS

This invention generally relates to a process for epoxidizing an olefin in an inert organic solvent in which all the reactants and catalyst components are soluble.

In particular, the invention relates to a process for epoxidizing a variety of ethylenically unsaturated compounds with a soluble catalyst system in a non-oxidizing alcoholic solvent.

The olefins useful in this process are those containing at least one ethylenic unsaturation. In general, any hydrocarbon olefin having from 2 to about 20 carbon atoms can be oxidized. The aliphatic hydrocarbon monoolefins include, for example, ethylene, propylene, butene-1, butene-2, isobutene, pentene-1, pentene-2, hexene, isohexene, heptene, 3-methylhexene, octene-1, isooctene, nonene, decene, dodecene, tridecene, pentadecene, octadecene, eicosene, docosane, etc. Examples of hydrocarbon diolefins which can also be oxidized include butadiene, pentadiene, hexadiene, octadiene, decadiene, tridecadiene, etc. The alicyclic hydrocarbon olefins can also be oxidized, such as for example, cyclopentene, cyclohexene, cycloheptene, methyl cyclohexene, isopropyl cyclohexene, butylcyclohexene, etc. Allylic compounds are very suitably oxidized by the instant process, such as for example, allyl alcohol and allyl chloride. It is known for several epoxidation systems that allyloxy-moieties lead to greatly diminished rates. The instant process is particularly suitable for oxidizing allyloxy-moieties, such as for example, substituted and unsubstituted phenylallylethers. Specific examples include phenyl allyl ether and the diallyl ether of bisphenol A (2,2-bis(4-hydroxyphenyl)propane). Epoxidation of the diallyl ether of bisphenol A provides a very satisfactory route to EPON ® resins.

Various compounds of molybdenum, tungsten and rhenium can be utilized as catalysts as long as they are soluble in the reaction medium, such as, for example anhydrides, acids, heteropoly acids, organic esters and complexes like acetylacetonates, etc. The catalyst compound is employed in the reaction mixture in an amount within a range of about 0.001 to about 1 g of catalyst metal per liter, preferably from about 0.01 to about 0.1. Excellent results can be obtained by the use of tungsten and molybdenum compounds derived from tungsten or molybdenum anhydrides, such as the hydrates of tungsten and molybdenum anhydride, the molybdic acid of Graham and Murgier, the esters of tungstic and molybdic acid, such as propylene glycol tungstate or molybdate, tungsten and molybdenum complexes, such as that with acetylacetone, heteropoly acids of tungsten or molybdenum, such as the phosphomolybdic acids or mixtures of these compounds. Other organo metallic compounds such as the naphthenates, the stearates, the octoates, the carbonyls and the like are also suitable. The preferred metal catalyst is tungstic acid ($H_2WO_4$).

The co-catalyst utilized in the instant process preferably will be an organo tin compound having at least 1 carbon atom, preferably from 1 to about 30 carbon atoms. In general, suitable organo tin compounds have been exemplified in U.S. Pat. No. 3,806,467, incorporated by reference herein. More particular examples are those having the general formula:

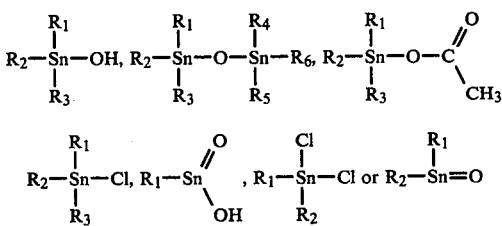

wherein each of $R_1$, $R_2$, $R_3$, $R_4$, $R_5$ and $R_6$ represents an alkyl group, aralkyl group, phenyl group, phenoxy group, alkoxy group, hydrogen atom, carbonyl group, nitrile group, hydroxyl group, acyl group, halogen group, —S—R or —O—R and R represents an alkyl or phenyl group. It is also possible to employ a synthesized solution or extract containing such tin compound. Compounds similar to the above but utilizing arsenic antimony or germanium instead of tin are also utilized.

The transition metal catalyst and the organo tin catalyst to be used in the present invention may be added simultaneously or mixed in advance to the reaction system or may be added separately to the reaction mixture.

For the concentration of the catalyst, each of the transition metal catalysts and the organo tin co-catalysts can be selected independently over a wide range. Although the ratio of the organo tin co-catalysts to the transition metal catalysts is not independent of the reaction products, the ratio may be varied widely. But, the atomic ratio of tin in the organo tin catalysts to the transition metal in the transition metal catalysts is preferably greater than 1. The tin to transition metal will range from about 1:1 to about 1000:1, preferably from about 1:1 to about 500:1, and more preferably from about 1:1 to about 200:1.

The alcoholic solvents utilized in the instant invention are linear fluorinated alcohols of the following general formula:

$$CF_3(CF_2)_nCH_2OH$$

where n ranges from 0 to about 10. Illustrative examples of the suitable alcohols are 2,2,2-trifluoroethanol-1, 2,2,3,3,3-pentafluoropropanol-1, 2,2,3,3,4,4,4-heptafluorobutanol-1 and the like.

There are several modes of carrying out the instant invention. For example, a solution can be prepared of hydrogen peroxide, fluorinated alcohol and catalysts and the olefin added subsequently, or a solution can be prepared of the fluorinated alcohol and the catalysts and olefin and hydrogen peroxide added thereto simultaneously. A preferred mode is to prepare a solution of olefin, fluorinated alcohol and catalysts and slowly add thereto hydrogen peroxide.

The hydrogen peroxide is normally added as an aqueous solution, usually a 50% by weight aqueous solution, but care should be taken to see that concentrations are used which maintain the total water content less than 25%, preferably less than 20% and most preferably less than about 15% based on the weight of the fluoro alcohol and aqueous peroxide including the water produced during the reaction.

The temperature of the reaction is kept in the range of about 20° C. to about 150° C., preferably from about 50° C. to about 90° C. The reaction time may vary from about 8 minutes to about 10 hours, preferably from about 0.5 hours to about 3 hours. The reaction pressure can be atmospheric, subatmospheric or super-atmospheric.

The process may be run in a batch mode or a step wise batch mode or a continuous mode where either one or both the olefin or hydrogen peroxide is added subsequent to initiation of the process.

Since there is no oxidation of the alcoholic solvent, this process is especially suited for a continuous reaction mode in which the olefin and hydrogen peroxide are added simultaneously.

Isolation of the resulting epoxide is generally accomplished by fractional distillation to yield a substantially pure epoxide in cases where the epoxide is relatively low boiling.

The following illustrative embodiments serve to illustrate the invention and are not to be construed as limiting the scope of the present invention.

ILLUSTRATIVE EMBODIMENTS

A 100-ml 3-neck round-bottom Morton flask equipped with a glass mechanical stirrer (Teflon paddle), condenser and addition funnel is utilized to carry out the illustrative embodiments described herein. The equipment is first carefully pacified to remove all traces of contaminants that might decompose hydrogen peroxide. The catalysts, co-catalysts, solvent and olefin are then weighed into the flask and the hydrogen peroxide is placed in the addition funnel. The reactor is heated by a controlled oil bath and the reaction is performed under nitrogen. Hydrogen peroxide analysis is performed by ceric sulfate titration. Conversion of olefin and expoxide yield are obtained by GLC.

A series of runs are made using phenylallylether as the olefin at a temperature of 70° C. with an hydrogen peroxide addition time of 2 hours. The results are shown in Table 1 below as Examples 1 and 2. For comparative purposes the use of other solvents as for example those exemplified by U.S. Pat. No. 3,806,467 are carried out and shown below as Examples 3, 4 and 5. It is clear from Table 1 that the linear fluorinated alcohols of the instant process give much higher olefin conversions than the non-fluorinated alcohols.

TABLE 1

| Example | Catalyst (moles) | Cocatalyst (moles) | Solvent | Conversion Olefin | Selec. based on HP | Selec. based on olefin | Comments |
|---|---|---|---|---|---|---|---|
| 1 | $H_2WO_4$ (0.0015) | $(CH_3)_3SnOH$ (0.005) | $CF_3CH_2OH$ | 48 | 35 | 96 | |
| 2 | $H_2WO_4$ (0.0015) | $(CH_3)_3SnOH$ (0.005) | $CF_3CH_2OH$ | 91 | ~10 | 93 | This work 10/1 olefin/$H_2O_2$ 4 hours |
| 3 | $MoO_2(AcAc)_2$ (0.0005) | $(CH_3)_3SnOH$ (0.005) | n-propanol | 2.1 | 2 | 85 | |
| 4 | $H_2WO_4$ (0.0015) | $(CH_3)_3SnOH$ (0.005) | EtOH | 20 | 7 | ~100 | |
| 5 | $H_2WO_4$ (0.0005) | $(CH_3)_3SnOH$ (0.005) | n-propanol | 13 | 6 | ~100 | |

Additional experiments and comparative examples are carried out at a temperature of about 70° C., a reaction time of about 2.5 hours, a hydrogen peroxide addition time of about 5 hours with the addition of 0.90 moles of 50% hydrogen peroxide. Results for these tests are shown in Table 2 below.

TABLE 2

| Example | Catalyst (mole) | Co-Catalyst (mole) | Olefin (mole) | Solvent (grams) | Olefin Conversion[a] (mole %) | Selectivity[a] to Epoxide (basis olefin) mole % |
|---|---|---|---|---|---|---|
| 6 | Tungstic Acid 0.0005 | Triphenyl tin OH 0.005 | APE[b] 0.046 | TFE[c] 41.70 | 46 | 95 |
| 7 | Tungstic Acid 0.0005 | n-butyl tin OH 0.005 | APE 0.046 | TFE 40.63 | 46 | ~100 |
| 8 | Tungstic Acid 0.0005 | $(CH_3)_3SnOH$ 0.005 | APE 0.046 | Ethanol 23.41 | 7 | 33 |

TABLE 2-continued

| Example | Catalyst (mole) | Co-Catalyst (mole) | Olefin (mole) | Solvent (grams) | Olefin Conversion[a] (mole %) | Selectivity[a] to Epoxide (basis olefin) mole % |
|---|---|---|---|---|---|---|
| 9 | Tungstic Acid 0.0005 | $(CH_3)_3SnOH$ 0.005 | APE 0.046 | n-propanol 23.57 | 9 | 44 |
| 10 | Tungstic Acid 0.0015 | $(CH_3)_3SnOH$ 0.005 | APE 0.046 | TFE 41.45 | 50 | 92 |
| 11 | Tungstic Acid 0.0005 | $(CH_3)_3SnOH$ 0.005 | APE 0.046 | TFE 40.28 | 26 | 75 |
| 12 | Molybdic Acid 0.0005 | $(CH_3)_3SnOH$ 0.005 | APE 0.046 | TFE 40.46 | 28 | ~100 |
| 13[d] | $MoO_2(AcAc)_2$ 0.0005 | $(CH_3)_3SnOH$ 0.005 | APE 0.046 | TFE 41.82 | 24 | ~100 |
| 14 | $MoO_2(AcAc)_2$ 0.0005 | $(CH_3)_3SnOH$ 0.005 | APE 0.046 | Ethanol 22.67 | 2 | 8 |
| 15 | Tungstic Acid 0.0015 | $(CH_3)_3SnOH$ 0.005 | APE 0.046 | TFE | 50 | 96 |
| 16 | $MoO_2(AcAc)$ 0.0005 | $(CH_3)_3SnOH$ 0.005 | APE 0.046 | n-propanol 22.67 | 2 | 12 |
| 17 | Tungstic Acid 0.0015 | $(CH_3)_3SnOH$ 0.005 | 1-octene 0.046 | TFE 40.73 | 65 | 73 |
| 18 | Tungstic Acid 0.0015 | $(CH_3)_3SnOH$ 0.005 | 1-octene 0.046 | n-propanol 23.26 | 11 | 38 |
| 19 | $NH_4ReO_4$ 0.0015 | $(CH_3)_3SnOH$ 0.005 | APE 0.046 | TFE 41.04 | 7 | ~100 |
| 20 | $NH_4ReO_4$ 0.075 | $(CH_3)_3SnOH$ 0.025 | APE 0.046 | TFE 43.12 | 7 | 60 |
| 21 | $NH_4ReO_4$ 0.0015 | $(CH_3)_3SnOH$ 0.005 | APE 0.046 | TFE 41.13 | 9 | 80 |
| 22 | Tungstic Acid 0.0015 | $(CH_3)_3SnOH$ 0.030 | APE 0.059 | TFE 42.29 | 15 | 64 |
| 23 | Tungstic Acid 0.0015 | $(CH_3)_3SnOH$ 0.015 | APE 0.046 | TFE 41.74 | 44 | ~100 |
| 24 | Tungstic Acid 0.0015 | $(CH_3)_3SnOH$ 0.005 | APE 0.046 | HFB[e] 46.82 | 35 | 80 |
| 25 | Tungstic Acid 0.0015 | $(CH_3)_3SnOH$ 0.005 | APE 0.046 | PFP[f] | 41 | ~100 |
| 26 | Tungstic Acid 0.0015 | $(C_6H_5)_3A_sO$ 0.005 | APE 0.046 | TFE 39.19 | 37 | 71 |
| 27 | Tungstic Acid 0.0015 | $C_6H_5A_sO$ 0.005 | APE 0.046 | TFE 40.57 | 28 | 56 |
| 28 | Tungstic Acid 0.0015 | $(C_6H_5)_3A_sO$ | APE 0.046 | TFE 40.77 | 37 | 85 |
| 29 | Tungstic Acid 0.0015 | $C_6H_5A_sO$ 0.015 | APE 0.046 | TFE 40.93 | 33 | 60 |

[a] by GLC
[b] APE = allyl phenyl ether
[c] TFE = 2,2,2-trifluoroethanol
[d] AcAc = acetylacetonate
[e] HFB = 4,4,4,3,3,2,2-heptafluorobutanol-1
[f] PEP = 3,3,3,2,2-pentafluoropropanol-1

I claim:

1. In the process for the production of epoxides by contacting a substituted or unsubstituted phenylallyl ether with hydrogen peroxide in an organic solvent in the presence of homogeneous transition metal catalyst selected from the group consisting of molybdenum, tungsten and rhenium and a homogeneous organo metallic co-catalyst selected from the group consisting of organo tin, organo arsenic, organo antimony and organo germanium, the improvement which comprises using as the organic solvent a fluorinated alcohol having the formula $CF_3(CF_2)_nCH_2OH$ where n ranges from 0 to about 10.

2. The process of claim 1 wherein the temperature ranges from about 50° C. to about 90° C.

3. The process of claim 1 wherein the organo metallic co-catalyst is tin.

4. The process of claim 1 wherein the ether is phenyl allyl ether.

5. The process of claim 1 wherein the ether is the diallyl ether of 2,2-bis(4-hydroxyphenyl)propane.